United States Patent
Takemura et al.

(10) Patent No.: US 6,900,225 B2
(45) Date of Patent: May 31, 2005

(54) QUINOLONECARBOXYLIC ACID DERIVATIVE

(75) Inventors: Makoto Takemura, Tokyo (JP);
Hisashi Takahashi, Tokyo (JP);
Katsuhiro Kawakami, Tokyo (JP);
Masao Itoh, Tokyo (JP); Tetsuya Suzuki, Tokyo (JP); Tsuyoshi Ohtani, Tokyo (JP); Masayasu Sekiguchi, Tokyo (JP); Rie Miyauchi, Tokyo (JP);
Isao Hayakawa, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/275,972

(22) PCT Filed: Mar. 30, 2001

(86) PCT No.: PCT/JP01/02761

§ 371 (c)(1),
(2), (4) Date: Mar. 31, 2003

(87) PCT Pub. No.: WO01/72738

PCT Pub. Date: Oct. 4, 2001

(65) Prior Publication Data

US 2003/0187008 A1 Oct. 2, 2003

(51) Int. Cl.$^7$ .................. A61K 31/4709; C07D 401/02
(52) U.S. Cl. .................. 514/312; 546/156; 546/153
(58) Field of Search .................. 514/312; 546/156, 546/153

(56) References Cited

U.S. PATENT DOCUMENTS 5,286,723 A    2/1994   Hayakawa et al.

FOREIGN PATENT DOCUMENTS

| EP | 341493 | 11/1989 |
|----|--------|---------|
| JP | 6-49059 | 2/1994 |
| JP | 6-199834 | 7/1994 |
| JP | 2714597 B2 | 11/1997 |
| JP | 2903292 B2 | 3/1999 |
| JP | 2000-26296 | 1/2000 |

*Primary Examiner*—Charanjit S. Aulakh
(74) *Attorney, Agent, or Firm*—Sughrue Mion, PLLC

(57) ABSTRACT

(−)-7-[(7S)-7-Amino-5-azaspiro[2.4]heptan-5-yl]-6-fluoro-1-[(1R, 2S)-2-fluoro-1-cyclopropyl]-1,4-dihydro-8-methoxy-4-oxo-3-quinolinecarboxylic acid.1HCl.1H$_2$O and antibacterial compositions containing this compound. The compound of the present invention exhibits not only excellent antibacterial activity and safety, but also remarkable stability against light and humidity, and is thus useful as an antibacterial agent.

6 Claims, 3 Drawing Sheets

QUINOLONECARBOXYLIC ACID DERIVATIVE

BACKGROUND OF THE INVENTION

1. Field of the Invention

The present invention relates to optically active quinolonecarboxylic acid derivatives which exhibit high antibacterial activity and safety and have remarkable stability, and to an antibacterial composition containing such a derivative.

2. Related Art

Quinolonecarboxylic acid derivatives are a class known as synthetic antibacterial agents. Particularly, compounds of the following formula (I) having a 1,2-cis-2-halogenocyclopropyl group on the nitrogen atom at the 1-position of the quinolone skeletone exhibit strong antibacterial activity and safety, and thus are known to be useful as pharmaceutical agents (Japanese patent No. 2714597 and 2917010);

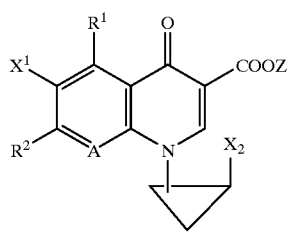

(I)

wherein $R^1$ is an amino group, a methylamino group, a hydroxyl group, a thiol group, or a hydrogen atom; and $R^2$ is a substituent selected from the group consisting of the following groups:

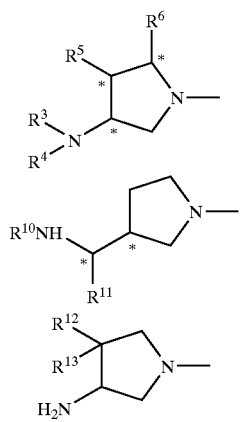

(wherein $R^3$, $R^4$, $R^5$, and $R^6$ each independently represents a hydrogen atom or a C1–C6 alkyl group, $R^{10}$ and $R^{11}$ each independently represents a hydrogen atom or a C1–C6 alkyl group, $R^{12}$ and $R^{13}$ each independently represents a hydrogen atom or a C1–C6 alkyl group or $R^{12}$ and $R^{13}$ may form a polymethylene chain of from 2 to 5 carbon atoms), or a 3-hydroxypyrrolidinyl group which may have a C1–C6 alkyl group; A represents C-$X^3$ or a nitrogen atom; $X^1$ and $X^2$ each independently represents a halogen atom; $X^3$ represents a halogen atom, a C1–C6 alkyl group, a C1–C6 alkoxy group, trifluoromethyl group, or a hydrogen atom; and Z represents a hydrogen atom, a C1–C6 alkyl group, a C1–C6 alkoxyalkyl group, a phenylalkyl group of C1–C6 alkyl, a phenyl group, an acetoxymethyl group, a pivaloyloxymethyl group, an ethoxycarbonyloxy group, a chorine group, a dimethylaminoethyl group, a 5-indanyl group, a phthalidinyl group, a 5-substituted-2-oxo-1,3-dioxol-4-ylmethyl group, or a 3-acetoxy-2-oxobutyl group; with the case in which $R^2$ is a 3-aminopyrrolidinyl group and $R^1$ and $X^3$ are hydrogen atoms being excluded.

A variety of fluoroquinolone synthetic antibacterial agents have been developed to provide clinical drugs for chemotherapy which are effective in the treatment of a broad range of systemic infectious diseases. Nevertheless, demands still exist for compounds which exhibit higher antibacterial activity, which are safer than the previous compounds, and in addition, which are endowed with excellent stability against light and humidity.

SUMMARY OF THE INVENTION

In view of the foregoing, the present inventors, focusing on $N_1$-(1,2-cis-2-fluorocyclopropyl)-substituted pyrrolidonecarboxylic acids disclosed in the aforementioned Japanese Patent No. 2714597, have performed further research and have found that a monohydrochloride•monohydrate of compound No. 41 disclosed in Japanese Patent No. 2714597—but the disclosure being limited only to the chemical formula of its free form, particularly, (−)-7-[(7S)-7-amino-5-azaspiro[2.4]heptan-5-yl]-6-fluoro-1-[(1R, 2S)-2-fluoro-1-cyclopropyl]-1,4-dihydro-8-methoxy-4-oxo-3-quinolinecarboxylic acid (hereinafter referred to as compound (1a); compound (1a) corresponds to a free form and is represented by the following formula (1a))—exhibits not only excellent antibacterial activity and safety, but also exceptionally excellent stability against light and humidity as compared with other acid-adduct salts, and is thus useful as an antibacterial agent. The present invention has been accomplished on the basis of these findings.

Accordingly, the present invention provides a compound represented by the following formula (1):

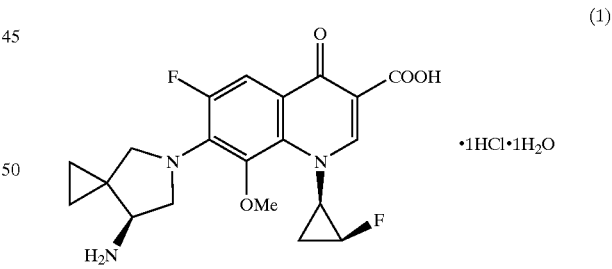

(1)

which is (−)-7-[(7S)-7-amino-5-azaspiro[2.4]heptan-5-yl]-6-fluoro-1-[(1R, 2S)-2-fluoro-1-cyclopropyl]-1,4-dihydro-8-methoxy-4-oxo-3-quinolinecarboxylic acid monohydrochloride monohydrate (hereinafter referred to as compound (1); compound (1) is a monohydrochloride-monohydrate of compound (1a)), and antibacterial agents containing the compound (1).

The present invention also provides an antibacterial agent containing a compound represented by the following formula (1a), an acid-adduct salt thereof, or a hydrate of the following formula (1a) compound or the acid-adduct salt.

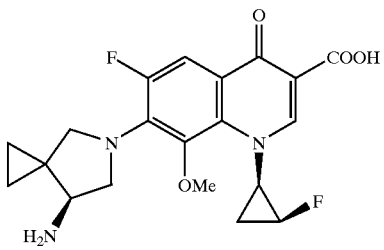

(1a)

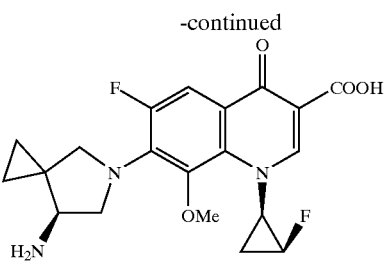

(1a)

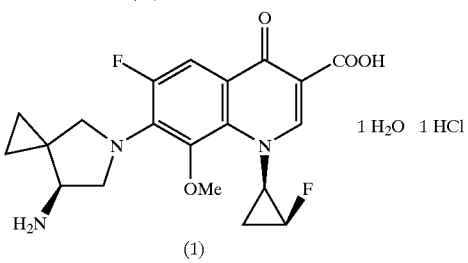

(1)

The present invention further provides use of the above-described compound of formula (1a), an acid-addition salt thereof, or a hydrate of the formula (1a) compound or the acid-addition salt in the manufacture of a drug for the treatment of infectious diseases.

DETAILED DESCRIPTION OF THE INVENTION AND PREFERRED EMBODIMENTS

Figure 1:
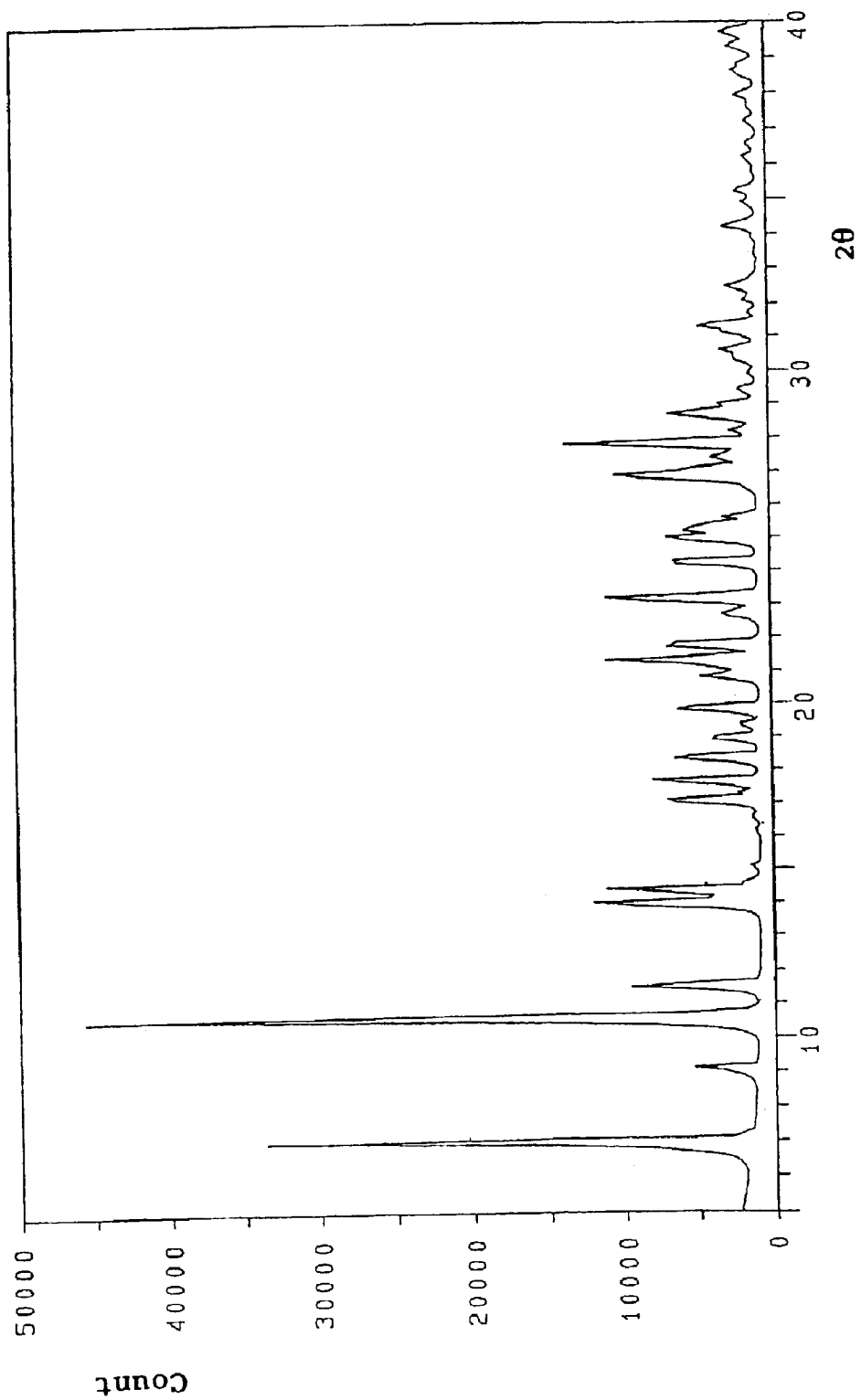
FIG. 1 shows a powder X-ray diffraction spectrum of compound (1).

Compound (1a) can be produced from a compound (2) at high yield in accordance with the following reaction scheme. Briefly, an amine compound (3) is reacted with compound (2) (note: both of these compounds can be obtained through the method described in Japanese Patent No. 2714597), and treatment of the resultant compound (1b) with a protic solvent yields compound (1a). Accordingly, compound (1b) is a useful synthetic intermediate in the production of compound (1a).

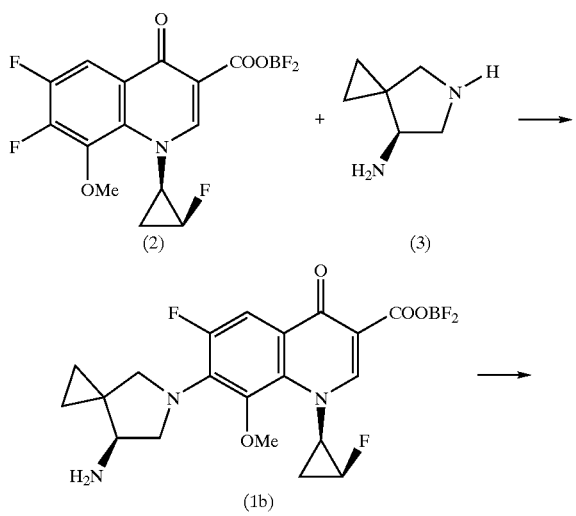

With regard to the reaction conditions under which compound (1b) is produced from compound (2), for example, a solution of dihydrochloride of amine (3) and triethylamine in dimethylsulfoxide is stirred (ordinary, for at most 2 to 3 hours is enough) at room temperature a solution of, and thereafter, compound (2) is added thereto and are reacted at room temperature for 10 minutes to several hours. In this reaction, instead of the dihydrochloride of amine (3), a corresponding free base (3) or a salt of any other type may be used. The salt of any other type may be, for example, monohydrochloride, or a mono- or di-salt—here, "mono-" and "di-" are both with respect to amine (3)—of organic or inorganic acid (other than HCl). Alternatively, the salt may be in the form of a hydrate or a solvate. Examples of the organic or inorganic acid suitable for acid-addudct salt(other than HCl) include sulfuric acid, nitric acid, hydrofluoric acid, hydrobromic acid, hydroiodic acid, p-toluenesulfonic acid, methanesulfonic acid, trifluoroacetic acid, trichloro-acetic acid, acetic acid, formic acid, maleic acid, and fumaric acid. Examples of the reaction solvent in addition to dimethylsulfoxide include N,N-dimethylformamide, N,N-dimethylacetamide, and N-methylpyrrolidone. In the above-mentioned example in which triethylamine is used, when a free base of amine (3) is employed, the amount of triethylamine is preferably one equivalent or more, more preferably two equivalents or more. When a salt of amine (3) is employed, the amount of triethylamine is preferably equal to or more than a total of the equivalent required for rendering the salt into a free base and the equivalent required for capturing hydrogen fluoride generated from the reaction. Instead of triethylamine, any other organic or inorganic bases, such as 4-(dimethylamino)pyridine or potassium carbonate, may be used.

The production step of compound (1a) from compound (1b) may be performed by, for example, dissolving compound (1b) in aqueous ethanol, adding triethylamine to the resultant mixture, followed by refluxing for a few hours. The aqueous ethanol may be replaced by another protic solvent, such as aqueous isopropanol. The protic solvents miscible with water are suitable for this process, and these which can at least dissolve compound (1b) when heated is preferable. Note that triethylamine is not necessarily added.

Compound (1a) may also be produced from a compound (2) at high yield in accordance with the following reaction scheme. Briefly, amine compound (5) is reacted with compound (2), to thereby obtain a carboxylic compound (7), and thereafter the protective group for the amino group is removed.

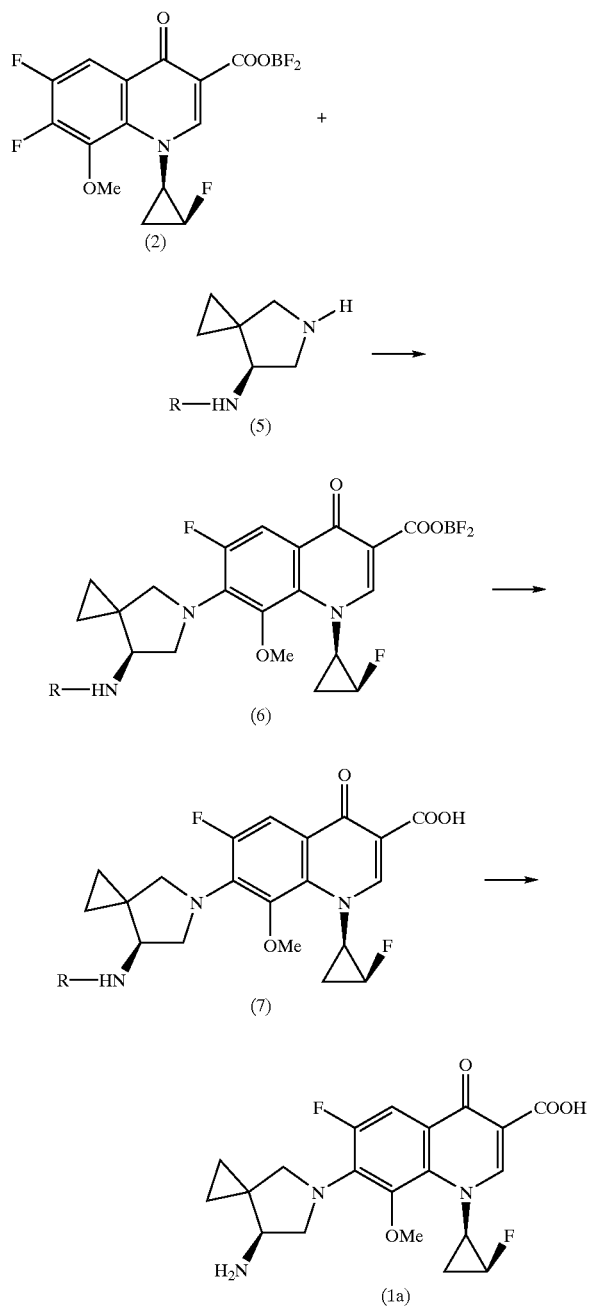

(wherein R represents an alkoxycarbonyl group, an aralkyloxycarbonyl group, an acyl group, an alkyl group, an aralkyl group, an alkoxyalkyl group (all of these may have substituent(s)), or a substituted silyl group). Accordingly, compounds (6) and (7) are useful as synthetic intermediates in the production of compound (1a).

In compound (6), R serves as a protective group for an amino group, and is an alkoxycarbonyl group which may have substituent(s), an aralkyloxycarbonyl group which may have substituent(s), an acyl group which may have substituent(s), an alkyl group which may have substituent(s), an aralkyl group which may have substituent(s), an alkoxyalkyl group which may have substituent(s), or a substituted silyl group. Of these species, R is preferably alkoxycarbonyl group, an aralkyloxycarbonyl group, an acyl group, or a silyl group, with alkoxycarbonyl and aralkyloxycarbonyl being more preferred. Specific examples of the alkoxycarbonyl group which may have substituent(s) include a tert-butoxycarbonyl group (Boc) and a 2,2,2-trichloroethoxycarbonyl group, wherein the tert-butoxycarbonyl group is preferred. Specific examples of the aralkyloxycarbonyl which may have substituent(s) group include a benzyloxycarbonyl group, a p-methoxybenzyloxycarbonyl group, and a p-nitrobenzyloxycarbonyl group, wherein the p-methoxybenzyloxycarbonyl group and the p-nitrobenzyloxycarbonyl group are preferred. Specific examples of the acyl group which may have substituent(s) include an acetyl group, a methoxyacetyl group, a trifluoroacetyl group, a chloroacetyl group, a pyvaloyl group, a formyl group, and a benzoyl group. Of these species, a trifluoroacetyl group, a chloroacetyl group, a pyvaloyl group, and a formyl group are preferred. Specific examples of the alkyl group which may have substituent(s) include a tert-butyl group. Examples of the aralkyl group which may have substituent(s) include a benzyl group, a p-nitrobenzyl group, p-methoxybenzyl group, and a triphenylmethyl group, with the p-methoxybenzyl group and triphenylmethyl group being preferred. Examples of the alkoxyalkyl group which may have substituent(s) include a methoxymethyl group, a tert-butoxymethyl group, a 2,2,2-trichloroethoxymethyl group, and a tetrahydrofuranyl group, with the tert-butoxymethyl group and tetrahydrofuranyl group being preferred. Examples of the substituted silyl group include a trimethylsilyl group, an isopropyldimethylsilyl group, a tert-butyldimethylsilyl group, a tribenzylsilyl group, and a tert-butyldiphenylsilyl group, with the isopropyldimethylsilyl group, a tert-butyldimethylsilyl group being preferred.

However, R is not limited only to the above-listed species, and any group which is ordinarily used for the protection of an amino group is suitable for the present invention and the protective group selected from the group consisting of alkoxycarbonyl groups, aralkyloxycarbonyl groups, acyl groups, alkyl groups, aralkyl groups, alkoxyalkyl groups, and silyl groups may serve as R.

With regard to the reaction conditions under which compound (6) is produced, for example, an amine (5) may be used to cause a reaction in dimethylsulfoxide in the presence of trimethylamine at room temperature for several hours to one day. Amine (5) may be in the form of a free base, or a salt of an organic or inorganic acid. Preferably, amine (5) is used in an mount of one equivalent or more. When a free base of amine (5) is used, a required amount of triethylamine is one or more equivalents, more preferably two or more equivalents. Alternatively, when a salt of amine (5) is employed, the amount of triethylamine is preferably equal to or more than a total of the equivalent required for rendering the salt into a free base, and further equivalent required for capturing hydrogen fluoride generated from the reaction. Examples of salts of amine (5) include salts of organic or inorganic acid, such as hydrochloric acid, sulfuric acid, nitric acid, hydrofluoric acid, hydrobromic acid, hydroiodic acid, p-toluenesulfonic acid, methanesulfonic acid, trifluoroacetic acid, trichloroacetic acid, acetic acid, formic acid, maleic acid, and fumaric acid. These salts may be in a form of hydrates or solvates. Examples of the reaction solvent in addition to dimethylsulfoxide include N,N-dimethylformamide, N,N-dimethylacetamide, and N-methylpyrrolidone. In the above-mentioned example in which triethylamine is used, the triethylamine may be replaced by any one of organic or inorganic bases, such as 4-(dimethylamino)pyridine or potassium carbonate.

Conversion of compound (6) to compound (7) may be performed by, for example, dissolving compound (6) in aqueous ethanol, adding triethylamine to the resultant mixture, followed by refluxing for a few hours. The aqueous ethanol may be replaced by another protonic solvent, such as aqueous isopropanol. The protic solvents miscible with water are suitable for this process, and these which can at least dissolve compound (1b) when heated is preferable. Note that triethylamine is not necessarily added.

In the step of producing compound (1a) from compound (7), the conditions under which the protective group R is removed must conform with the properties of the protective group R. Typical exemplary cases are as follows. When R is a tertbutoxycarbonyl group (Boc), deprotection may be carried out through treatment with an organic or inorganic acid such as hydrochloric acid, sulfuric acid, nitric acid, hydrofluoric acid, hydrobromic acid, hydroiodic acid, p-toluenesulfonic acid, methanesulfonic acid, trifluoroacetic acid, trichloroacetic acid, acetic acid, or formic acid. The temperature at which deprotection is carried out is suitably chosen from the range of −30 to 100° C., in accordance with the type and concentration of the acid employed and with the property of the solvent. Similarly, deprotection may be carried out for a p-methoxybenzyloxycarbonyl group, an acetyl group, a pyvaloyl group, a methoxyacetyl group, a formyl group, a tert-butyl group, a methoxymethyl group, a tert-butoxymethyl group, a tetrahydrofuranyl group, a trimethylsilyl group, a triphenylmethyl group, or from similar groups through treatment with an acid that is suitably chosen from among hydrochloric acid, sulfuric acid, nitric acid, hydrofluoric acid, hydrobromic acid, hydroiodic acid, p-toluenesulfonic acid, methanesulfonic acid, trifluoroacetic acid, and trichloroacetic acid. A 2,2,2-trichloroethoxycarbonyl group and a 2,2,2-trichloroethoxymethyl group may be removed by using a combination of zinc and an acid (HCl or acetic acid). Deprotection of a benzyloxycarbonyl group, a p-methoxybenzyloxycarbonyl group, a p-nitrobenzyloxycarbonyl group, a benzyl group, a p-nitrobenzyl group, a p-methoxybenzyl group, or a triphenylmethyl group can be carried out through catalytic reduction. Acyl groups such as an acetyl group, a methoxyacetyl group, a trifluoroacetyl group, a chloroacetyl group, a pyvaloyl group, a formyl group, and a benzoyl group may be removed through treatment with an acid such as HCl or an alkali such as NaOH. Silyl groups such as a trimethylsilyl group, an isopropyldimethylsilyl group, a tert-butyldimethylsilyl group, a tribenzylsilyl group, and a tert-butyldiphenylsilyl group may be removed by use of an acid or fluoride ions. In this case, example of the acid include acetic acid, hydrochloric acid, and hydrofluoric acid, and a suitable acid must be chosen so as to be in conformity with the properties of the silyl group. As for the source of the fluoride ions, tetrabutylammonium fluoride may be used. A chloroacetyl group can be removed by use of thiourea. Details of the conditions under which deprotection is carried out are ordinary ones and not particularly limited.

With reference to compound (6), when R is a tert-butoxycarbonyl group or a similar group which can be removed by an acid, compound (1a) can be obtained through direct treatment of compound (6) with an organic or inorganic acid such as hydrochloric acid, sulfuric acid, nitric acid, hydrofluoric acid, hydrobromic acid, hydroiodic acid, p-toluenesulfonic acid, methanesulfonic acid, trifluoroacetic acid, or trichloroacetic acid.

In the above-described two production methods, compound (1a) may be obtained in a free form or as a salt. Examples of the salt include a salt of an inorganic or organic acid, such as hydrochloric acid, sulfuric acid, nitric acid, hydrofluoric acid, hydrobromic acid, hydroiodic acid, p-toluenesulfonic acid, methanesulfonic acid, trifluoroacetic acid, trichloroacetic acid, acetic acid, maleic acid, or fumaric acid; and a salt of an alkali or alkaline earth metal such as sodium, potassium, calcium, or lithium. In either case of compound (1a) being in its free form or a salt, the compound (1a) may be obtained in the form of a solvate. Examples of the solvate include those formed with water, ethanol, propanol, acetonitrole, or acetone; and hydrates which may be formed through absorption of moisture in air.

The compound (2) which is used in the aforementioned two reaction schemes for producing compound (1a) may be prepared through the following reaction path.

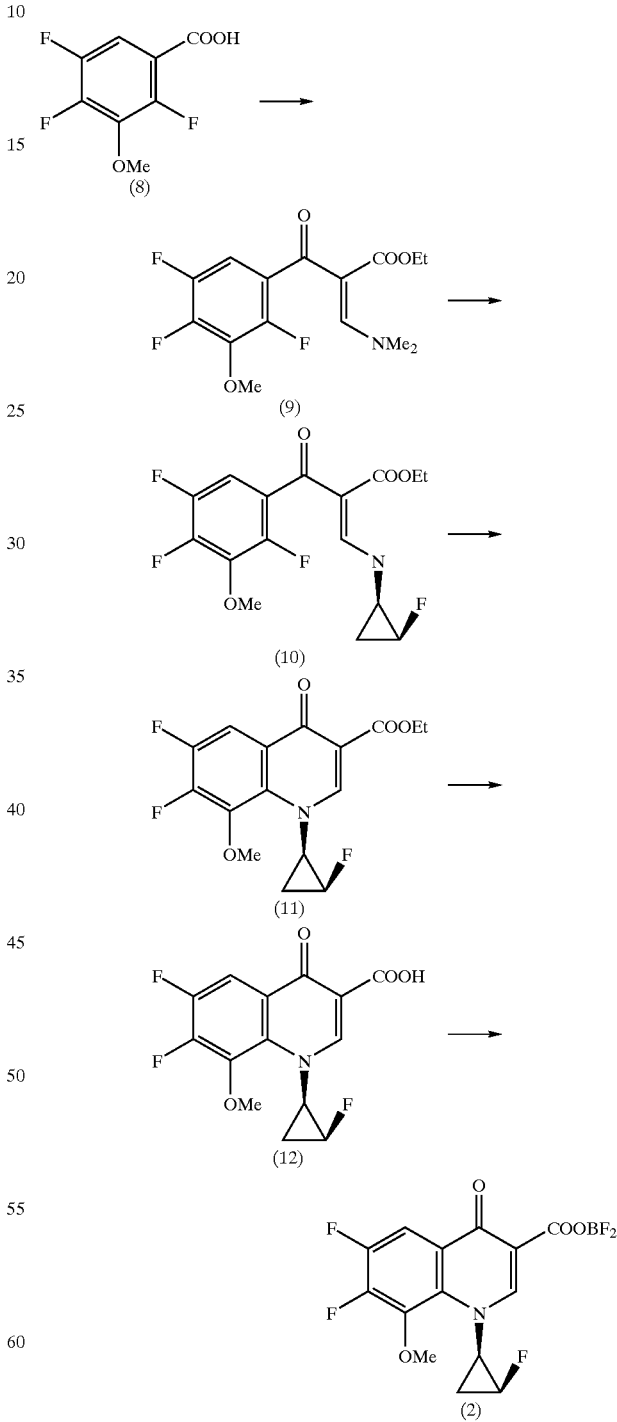

In the above scheme, in order to produce compound (2) from compound (12), an ether complex of boron trifluoride may be used. Alternatively, compound (2) may be obtained without obtaining compound (12) but by treating compound (11) with tetrafluoroboric acid as shown below.

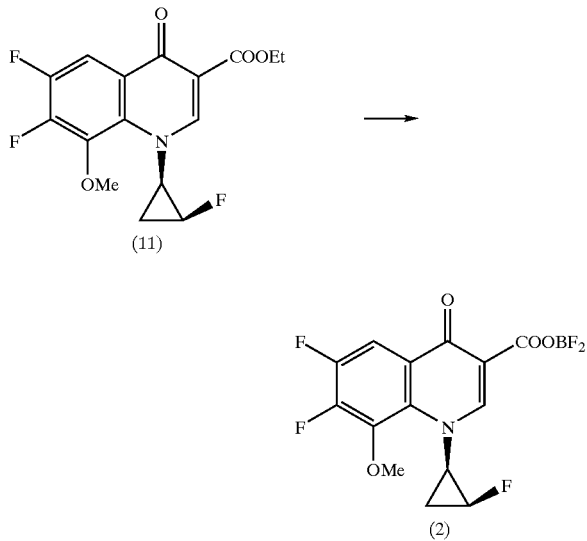

Conversion from compound (1a) to compound (1) can be carried out by, for example, suspending compound (1a) in an alcoholic solvent such as 2-propanol or ethanol, dissolving the suspension by the addition of HCl, and subsequently crystallizing from an alcoholic solvent such as 2-propanol or ethanol.

The thus-obtained compounds (1a), their acid-addition salts, or salts of the compounds (1a), in particular compounds (1), which are monohydrochlorides.monohydrates of compounds (1a), exhibit more excellent antibacterial activity and higher stability against light and humidity than, let alone other compounds, compound Nos. 9a, 9b, 13b, 18a, 18b, 26bb, 26aa, 26ba, 26ab, 31a, 31b, 34b, 54b, 56b, 52bb, or 85bb disclosed in Japanese Patent No. 2714597 or 2917010, and are thus useful as antibacterial agents. Preferred acid-addition salts of compounds (1a) applicable for antibacterial agents are hydrochloric acid salts. Among the mentioned compounds (1a), their acid-addition salts, and salts of the compounds (1a) or the acid-addition salts, compounds (1) are particularly preferred.

More preferred compounds (1); i.e., monohydrochlorides-.monohydrates of compounds (1a), are those exhibiting characteristic peaks in the vicinity of angles of diffraction (2θ) of 6.9, 10.5, 14.4, 23.1, 26.9, and 27.8(°) when subjected to powder X-ray diffractometry (see FIG. 1). The compounds (1) satisfying the above conditions do not absorb or desorb moisture under humidity conditions of 5 to 95% RH, and thus has excellent hygroscopic stability.

The compounds of the present invention, exhibiting strong antibacterial activity and excellent stability against light and humidity, are useful as pharmaceuticals for the treatment of humans, animals, and fish.

When the compounds of the present invention are used as pharmaceuticals for humans, the daily dose for an adult is from 50 mg to 1 g, preferably from 100 mg to 300 mg. When the compounds are administered to animals, the dose may vary depending on the purpose of administration (therapeutic or preventive), the species and size of the animal to be treated, the nature of the pathogen that infected the animal, and the severity of the pathological condition. However, the daily dose is typically from 1 mg to 200 mg, preferably from 5 mg to 100 mg, per kg of the body weight of the animal. This dose is administered once a day or 2–4 divided times a day. The daily dose may exceed the above-mentioned ranges.

Antibacterial compositions containing the aforementioned compounds of the present invention can be formulated in a variety of formulations through any ordinary methods in accordance with the manner of the administration. Examples of the peroral form of the antibacterial formulations containing the compound of the present invention as an active ingredient include tablets, powders, granules, capsules, solutions, syrups, elixirs, and oil-based or water-based suspensions.

Injections may contain a stabilizer, a preservative, or a solubilizing agent. Therefore, a solution which may contain any of these auxiliary agents may be placed in a container, and a solid preparation may be formulated through, for example, freeze-drying, thereby yielding a pharmaceutical product for bed-side preparation. Moreover, one dose or a plurality of doses may be contained in a single container.

When the composition of the present invention is formulated into external agents, examples of the external agents include solutions, suspensions, emulsions, ointments, gels, creams, lotions, and sprays.

Solid preparations may contain, in addition to the compound of the present invention, pharmaceutically acceptable additives including fillers, volume-increasing agents, binders, disintegrants, dissolution accelerators, wetting agents, and lublicants, as needed.

Examples of liquid preparations include solutions, suspensions, and emulsions. Liquid preparations optionally contain suspension aids and emulsifiers as additives therefor.

EXAMPLES

The present invention will be described in more detail by way of examples, which should not be construed as limiting the invention thereto.

Referential Example 1

Ethyl 3-dimethylamino-2-(3-methoxy-2,4,5-trifluorobenzoyl) acrylate:

Thionyl chloride (109.4 ml; 1500 mmol) was added dropwise at room temperature to a suspension containing 3-methoxy 2,4,5-trifluorobenzoic acid (206.1 g; 1000 mmol), N,N-dimethylformamide (2 ml), and toluene (2000 ml). After completion of the addition, the reaction mixture was stirred in an oil bath at 80° C. for 16 hours. The reaction mixture was cooled, and the cooled solution was concentrated under reduced pressure. Toluene was added to the residue, and the mixture was concentrated again. The procedure from the toluene addition to the concentration was repeated two more times, to thereby yield an acid chloride.

Ethyl 3-dimethylamino acrylate (171.8 g; 1200 mmol) and triethylamine (184.0 ml; 1320 mmol) were added to dry tetrahydrofuran (1500 ml). To the solution, a solution of the above-prepared acid chloride in dry tetrahydrofuran (500 ml) was added dropwise under ice cooling. After completion of the addition, the reaction suspension was refluxed for 5 hours, followed by cooling. The cooled reaction mixture was concentrated under reduced pressure, and water (1500 ml) and dichloromethane (1500 ml) were added to the residue, followed by stirring. The dichloromethane layer was collected, and the aqueous layer was extracted with dichloromethane (1000 ml). The combined dichloromethane layer was washed with saturated brine (1500 ml), and dried over anhydrous sodium sulfate, followed by filtration. The filtrate was concentrated under reduced pressure, and the residue was subjected to silica gel column chromatography. Fractions eluted with n-hexane/ethyl acetate (1:1) were concentrated, followed by drying under reduced pressure, to thereby yield 270.3 g of the title compound as yellowish white creamy matter (yield: 81.6%).

$^1$H-NMR(400 MHz, CDCl$_3$)δ: 1.02(3H, t, J=7.08 Hz), 2.88(3H, br), 3.32(3H, br), 4.00(2H, q, J=7.08 Hz), 7.09–7.13(1H, m), 7.83(1H, s).

Referential Example 2

Ethyl 3-[(1R, 2S)-2-fluoro-1-cyclopropylamino]-2-(3-methoxy-2,4,5-trifluorobenzoyl) acrylate:

Ethyl 3-dimethylamino-2-(3-methoxy-2,4,5-trifluorobenzoyl) acrylate (260.5 g; 786.3 mmol) was dissolved in dichloromethane (2200 ml), and (1R, 2S)-2-fluoro-1-cyclopropylamine p-toluene sulfonate (223.6 g; 904.2 mmol) was added to the solution. The resultant suspension was cooled to −15° C., and a solution of triethylamine (138.6 ml; 994.6 mmol) in dichloromethane (300 ml) was added dropwise to the suspension over 40 minutes while being stirred. After completion of the addition, the temperature was maintained for 1 hour, and then the suspension was cooled on ice for 1 hour, followed by stirring at room temperature for 14 hours. Dichloromethane (1000 ml) and water (2000 ml) were added to the reaction mixture, and the dichloromethane layer was collected. The aqueous layer was extracted with dichloromethane (500 ml), and the combined organic layer was washed with saturated brine (1000 ml), followed by drying over anhydrous sodium sulfate. The mixture was filtered, and the filtrate was concentrated under reduced pressure, to thereby yield 227.5 g of the title compound as yellow creamy matter (yield: 97.7%). The reaction product was a mixture of geometrical isomers (E and Z isomers). The product was used for the subsequent reaction without further purification.

$^1$H-NMR(400 MHz, CDCl$_3$)δ: 0.97, 1.09(total 3H, each t, J=7.08 Hz), 1.21–1.37(2H, m), 2.90–2.99(1H, m), 4.01(3H, s), 4.03, 4.06(total 2H, each q, J=7.08 Hz), 4.73(1H, dm, J=63.72 Hz), 6.86–6.92, 6.98–7.04 (total 1H, each m), 8.16, 8.23(total 1H, each d, J=13.67 Hz)

Referential Example 3

Ethyl 6,7-difluoro-1-[(1R, 2S)-2-fluoro-1-cyclopropyl]-1,4-dihydro-8-methoxy-4-oxo-3-quinoline carboxylate:

The above-synthesized crude ethyl 3-[(1R, 2S)-2-fluoro-1-cyclopropylamino]-2-(3-methoxy-2,4,5-trifluorobenzoyl) acrylate (276.2 g; 764.5 mmol) was dissolved in dry N,N-dimethylformamide (2000 ml), and potassium carbonate (317.0 g; 2.293 mmol) was suspended in the solution under ice cooling, followed by stirring for 72 hours at room temperature. Hydrochloric acid (2N) was added dropwise slowly to the reaction mixture so as to adjust the pH of the resultant suspension to about 3 while the suspension was stirred under ice cooling. The suspension was stirred for 30 minutes at room temperature, and crystals precipitated were collected by filtration. The thus-obtained crystals were sequentially washed with an excessive amount of purified water, a small amount of cold ethanol, and an excessive amount of diethylether, followed by drying under reduced pressure at 70° C., to thereby yield 213.4 g of the title compound as a white powder (yield: 81.8%).

$^1$H-NMR(400 MHz, CDCl$_3$)δ: 1.41(3H, t, J=7.08 Hz), 1.56–1.68(2H, m), 3.83–3.88(1H, m), 4.10(3H, d, J=2.20 Hz), 4.39(2H, q, J=7.08 Hz), 4.85(1H, dm, J=62.99 Hz), 8.05(1H, dd, J=8.55, 10.01 Hz), 8.57(1H, d, J=1.22 Hz).

Referential Example 4

6,7-Difluoro-1-[(1R, 2S)-2-fluoro-1-cyclopropyl]-1,4-dihydro-8-methoxy-4-oxo-3-quinolinecarboxylic acid:

A mixture of ethyl 6,7-difluoro-1-[(1R, 2S)-2-fluoro-1-cyclopropyl]-8-methoxy-1,4-dihydro-4-oxoquinoline-3-carboxylate (120.8 g; 354.1 mmol), glacial acetic acid (210 ml), and conc. hydrochloric acid (420 ml) was refluxed for 6 hours, followed by cooling. The cooled reaction mixture was poured into ice/water (1500 ml) while being stirred, and the mixture was stirred for an additional 30 minutes at room temperature. Crystals precipitated were collected by filtration, and the crystals were sequentially washed with an excessive amount of purified water, ethanol (300 ml), and diethyl ether (500 ml). The crystals were purified through recrystallization from ethanol-acetone (also through treatment with activated carbon and filtration), followed by drying under reduced pressure at 70° C., to thereby yield 107.0 g of the title compound as white needles (yield: 96.5%).

$^1$H-NMR(400 MHz, CDCl$_3$)δ: 1.64–1.75(2H, m), 3.97–4.00(1H, m), 4.17(3H, d, J=2.20 Hz), 4.91(1H, dm, J=63.23 Hz), 8.05(1H, dd, J=8.55, 10.01 Hz), 8.84(1H, s), 14.31(1H, s).

Referential Example 5

6,7-Difluoro-1-[(1R, 2S)-2-fluoro-1-cyclopropyl]-1,4-dihydro-8-methoxy-4-oxo-3-quinolinecarboxylic acid difluoroboron chelate:

6,7-Difluoro-1-[(1R, 2S)-2-fluoro-1-cyclopropyl]-1,4-dihydro-8-methoxy-4-oxo-3-quinolinecarboxylic acid (90.30 g; 288.3 mmol) was suspended in dry diethylether (1000 ml), and boron trifluoride/diethylether complex (653 ml) was added dropwise to the suspension under ice cooling. After completion of the addition, the reaction suspension was stirred for 24 hours at room temperature, and crystals precipitated were collected by filtration, followed by washing with an excessive amount of dry diethylether. The washed crystals were dried under reduced pressure at room temperature, to thereby yield 96.47 g of the title compound as a white powder (92.7%).

$^1$H-NMR(400 MHz, CDCl$_3$)δ: 1.77–1.98(2H, m), 4.30 (3H, d, J=2.93 Hz), 4.38–4.44(1H, m), 5.03(1H, dm, J=62.50 Hz), 8.17(1H, dd, J=8.06, 8.79 Hz), 9.14(1H, s).

Referential Example 6

6,7-Difluoro-1-[(1R, 2S)-2-fluoro-1-cyclopropyl]-1,4-dihydro-8-methoxy-4-oxo-3-quinolinecarboxylic acid difluoroboron chelate (alternative synthesis method):

A mixture of ethyl 6,7-difluoro-1-[(1R, 2S)-2-fluoro-1-cyclopropyl]-1,4-dihydro-8-methoxy-4-oxo-3-quinolinecarboxylate (260 mg; 0.733 mmol) and tetrafluoro boric acid (42%: 5 ml) was stirred in an oil bath at 90° C. for 3 hours. The reaction mixture was cooled, and an excessive amount of purified water was added to the solution. Crystals that precipitated were collected by filtration, and sequentially washed with purified water (excess amount) and diethylether (excess amount). The crystals were collected by filtration, and dried under reduced pressure at room temperature, to thereby yield 241 mg of the title compound as a white powder (yield: 91.1%). The $^1$H-NMR data of the reaction product was in agreement with the data of that synthesized in accordance with other synthesis methods.

Example 1

(−)-7-{(7S)-7-Amino-5-azaspiro[2.4]heptan-5-yl}-6-fluoro-1-[(1R, 2S)-2-fluoro-1-cyclopropyl]-1,4-dihydro-8-methoxy-4-oxo-3-quinolinecarboxylic acid (Compound 1a):

(7S)-7-Amino-5-azaspiro[2.4]heptane dihydrochloride (61.4 g; 0.332 mol) was dissolved in dimethylsulfoxide (800 ml), and triethylamine (138 ml; 0.994 mol) was added to the resultant solution under a nitrogen atmosphere at room temperature, followed by stirring for 10 hours. 6,7-Difluoro- 1-[(1R, 2S)-2-fluoro-1-cyclopropyl]-1,4-dihydro-8-methoxy-4-oxo-3-quinolinecarboxylic acid difluoroboron chelate (100 g; 0.276 mol) in powder form was slowly added to the reaction mixture, followed by stirring for 40 hours at room temperature. The reaction mixture was concentrated under reduced pressure, and ethanol (90%: 1000 ml) and triethylamine (20 ml) were added thereto, followed by refluxing for 2.5 hours. The reaction mixture was left to cool, and crystals that precipitated were collected by filtration. The crystals were sequentially washed with ethanol and ether, followed by drying under reduced pressure at 70° C. for 16 hours, to thereby yield 72.5 g of the title compound (as 0.5 hydrate) as a pale yellow powder (yield: 61.4%). Solvents were removed from the filtrate under reduced pressure, and water (2000 ml) was added to the residue. An aqueous sodium hydroxide solution (3N) was added to the mixture so as to adjust the pH value to 10.0 while being stirred under ice cooling. Subsequently, an aqueous hydrochloric acid solution (3N) was added to the mixture so as to adjust the pH to 7.4, followed by stirring for 16 hours at room temperature. Crystals that precipitated were collected by filtration, washed with water, and dried under reduced pressure at 70° C., to thereby yield 19.2 g of the title compound (as 0.5 hydrate) as a pale yellow powder (yield: 33.6%).

$^1$H-NMR(400 MHz, 0.1N NaOD)δ: 0.53–0.59(2H, m), 0.62–0.66(1H, m), 0.78–0.82(1H, m), 1.38–1.60(2H, m), 3.07(1H, s), 3.39(1H, dd, J=10.3, 26.0 Hz), 3.52(3H, s), 3.72(1H, d, J=10.0 Hz), 3.89–4.00(2H, m), 4.93(1H, dm, J=64.2 Hz), 7.62(1H, d, J=14.2 Hz), 8.43(1H, s).

Elementary analysis: on the basis of $C_{20}H_{21}F_2N_3O_4 \cdot 0.5H_2O$

Calculated: C, 57.97; H, 5.35; N, 10.14. Found: C, 57.97; H, 5.31; N, 10.11.

Specific rotation: $[\alpha]_D^{22}$–25.5°(c=0.832, 0.1N NaOH).
Melting point: 207–209° C.

Example 2

(−)-7-{(7S)-7-amino-5-azaspiro[2.4]heptan-5-yl}-6-fluoro-1-[(1R, 2S)-2-fluoro-1-cyclopropyl]-1,4-dihydro-8-methoxy-4-oxo-3-quinolinecarboxylic acid monohydrochloride monohydrate (Compound 1):

In a 3-liter teardrop flask, crystalline (−)-7-[(7S)-7-amino-5-azaspiro[2.4]heptan-5-yl]-6-fluoro-1-[(1R, 2S)-2-fluoro-1-cyclopropyl]-1,4-dihydro-8-methoxy-4-oxo-3-quinolinecarboxylic acid 0.5 hydrate (61.3 g; 148 mmol: calculated based on the free form: 60.0 g) was suspended in 2-propanol (720 ml). Subsequently, hydrochloric acid (5N: 59.2 ml; 296 mmol) was slowly added dropwise to the suspension while being stirred under ice cooling. The thus-obtained mixture was brought to room temperature, and distilled water (420 ml) was added thereto, followed by stirring for 10 minutes. The mixture was heated to 60° C. in a water bath while being stirred. After the suspension turned into a transparent solution, activated carbon (3 g) was added thereto, and the admixture was stirred for 20 minutes at an external temperature of 80° C. The activated carbon was filtered off, and the filtrate was concentrated under reduced pressure, followed by concentrated to driness through evaporation. The residue was dried in a water bath at 70° C. for 1 hour by use of a vacuum pump, and 2-propanol (96%: 1800 ml) was added thereto, followed by stirring in a water bath at 80° C. After a homogenous (clear) solution was obtained, the solution was stirred at 60° C. After a while, crystals began to precipitate, when the temperature of the water bath was brought to 25° C. over about 1.5 hours, followed by slow stirring for 20 hours. Crystals that precipitated were collected by filtration, washed with 2-propanol, and dried under reduced pressure at 70° C., to thereby yield 56.3 g of the title compound as pale yellow crystals (yield: 82.7%).

$^1$H-NMR(400 MHz, 0.1N NaOD)δ: 0.57–0.70(3H, m), 0.81–0.85(1H, m), 1.40–1.64(2H, m), 3.13(1H, t, J=4.39 Hz), 3.46(1H, dd, J=10.5, 24.6 Hz), 3.60(3H, s), 3.84(1H, dd, J=7.81, 10.3 Hz), 3.99–4.06(2H, m), 5.01(1H, dm, J=64.5 Hz), 7.66(1H, d, J=14.1 Hz), 8.42(1H, d, J=1.95 Hz).

Elementary analysis: on the basis of $C_{20}H_{21}F_2N_3O_4 \cdot 1.0HCl \cdot 1H_2O$ Calculated: C, 52.24; H, 5.26; N, 9.14. Found: C, 52.15; H, 5.25; N, 9.07.

Specific rotation: $[\alpha]_D^{22}$–166.5° (c=0.990, H$_2$O).
Melting point: 199–208° C.

Example 3

(−)-7-{(7S)-7-Amino-5-azaspiro[2.4]heptan-5-yl}-6-fluoro-1-[(1R, 2S)-2-fluoro-1-cyclopropyl]-1,4-dihydro-8-methoxy-4-oxo-3-quinolinecarboxylic acid-difluoroboron chelate (1b):

(7S)-7-Amino-5-azaspiro[2.4]heptane dihydrochloride (615 mg; 3.32 mmol) and triethylamine (1.40 ml) in dimethylsulfoxide (5 ml) was stirred for 20 minutes at room temperature. 6,7-Difluoro-1-[(1R, 2S)-2-fluoro-1-cyclopropyl]-1,4-dihydro-8-methoxy-4-oxo-3-quinolinecarboxylic acid difluoroboron chelate (1.00 g; 2.77 mmol) was added thereto, and the resultant mixture was stirred for 20 hours at room temperature. The reaction mixture was concentrated under reduced pressure, and purified water (50 ml) was added thereto. The pH of the resultant mixture was adjusted to 7.0 with aqueous 1N NaOH solution, and the aqueous layer of the mixture was taken up with chloroform (100 ml×5). The organic layer was dried over sodium sulfate, and the solvent was evaporated. The residue was purified through recrystallization from ethanol, to thereby yield 1.14 g of the title compound as pale yellow crystals (yield: 91%).

$^1$H-NMR (400 MHz, CDCl$_3$)δ: 0.65–0.73(3H, m), 0.82–0.86(1H, m), 1.50–1.60(1H, m), 1.66–1.76(1H, m), 3.25–3.27(1H, m), 3.45–3.58(2H, m), 3.69(3H, s), 4.00–4.03(1H, m), 4.12–4.15(1H, m), 4.19–4.24(1H, m), 4.95(1H, dm, J=62.7 Hz), 7.91(1H, d, J=13.7 Hz), 8.85(1H, d, J=2.20 Hz).

IR(KBr disk) cm$^{-1}$: 3396, 3080, 3001, 2941, 2883, 1716, 1631, 1560, 1522, 1441, 1363, 1331, 1288, 1257, 1225.

Melting point: 194–197° C. (decomposed)

Elementary analysis: on the basis of $C_{20}H_{20}BF_4N_3O_4 \cdot 0.25H_2O$

Calculated: C, 52.48; H, 4.51; N, 9.18. Found: C, 52.33; H, 4.36; N, 9.01.

Specific rotation: $[\alpha]_D^{19.7}$=−29.3°(c=1.03, DMF)

Example 4

(−)-7-{(7S)-7-Amino-5-azaspiro[2.4]heptan-5-yl}-6-fluoro-1-[(1R, 2S)-2-fluoro-1-cyclopropyl]-1,4-dihydro-8-methoxy-4-oxo-3-quinolinecarboxylic acid (1):

(−)-7-{(7S)-7-Amino-5-azaspiro[2.4]heptan-5-yl}-6-fluoro-1-[(1R, 2S)-2-fluoro-1-cyclopropyl]-1,4-dihydro-8-methoxy-4-oxo-3-quinolinecarboxylic acid difluoroboron chelate (1.14 g; 2.52 mol) was dissolved in 80% hydrated ethanol (100 ml; prepared by mixing 4 volumes of ethanol and one volume of water). Triethylamine (2 ml) was added thereto and the resultant mixture was subjected to reflux for 3 hours. The solvent was evaporated, and the residue was dissolved by the addition of concentrated HCl (5 ml) and 1N—HCl (5 ml), followed by washing with chloroform (100 ml×3). The pH of the resultant acidic solution was adjusted to 8.0 in an ice bath with aqueous 10N NaOH solution and aqueous 1N NaOH solution, followed by stirring for three hours at room temperature (pH after completion of stirring= 7.5). Crystals precipitated were collected by filtration and dried under reduced pressure, to thereby yield 980 mg of a crude form of the title compound as pale yellow crystals. The crystals were purified through recrystallization from a mixture of 28% ammonia water and ethanol, then dried under reduced pressure, yielding 561 mg of the title compound as yellowish white crystals (yield: 55%).

$^1$H-NMR (400 MHz, 0.1N—NaOD) δ: 0.53–0.59(2H, m), 0.62–0.66(1H, m), 0.78–0.82(1H, m), 1.38–1.60(2H, m), 3.07(1H, s), 3.39(1H, dd, J=10.3, 26.0 Hz), 3.52(3H, s), 3.72(1H, d, J=10.0 Hz), 3.89–4.00(2H, m), 4.93(1H, dm, J=64.2 Hz), 7.62(1H, d, J=14.2 Hz), 8.43(1H, s).

Example 5

7-[(7S)-5-Aza-7-tert-butoxycarbonylaminospiro[2.4]heptan-5-yl]-6-fluoro-1-[(1R, 2S)-2-fluoro-1-cyclopropyl]-1,4-dihydro-8-methoxy-4-oxo-3-quinolinecarboxylic acid difluoroboron chelate:

To 6,7-difluoro-1-[(1R, 2S)-2-fluoro-1-cyclopropyl]-1,4-dihydro-8-methoxy-4-oxo-3-quinolinecarboxylic acid difluoroboron chelate (1.00 g; 2.77 mmol) in dimethylsulfoxide (5 ml), (7S)-5-aza-7-tert-butoxycarbonylaminospiro[2.4]heptan (706 mg; 3.32 mmol) and triethylamine (927 μl) were added. The resultant mixture was stirred at room temperature for 20 hours. The reaction mixture was concentrated under reduced pressure, and purified water (40 ml) was added to the residue. Crystals precipitated were washed sequentially with purified water and a small amount of diethyl ether. The thus-washed crystals were dissolved in chloroform (100 ml), and the resultant solution was washed with water (50 ml×2) and saturated brine (50 ml). The organic layer was dried over sodium sulfate, and the solvent was evaporated. The thus-obtained crude product was purified through recrystallization from a mixture of n-hexane and ethanol, followed by drying under reduced pressure, to thereby yield 1.47 g of the title compound as pale yellow crystals (yield: 96%).

$^1$H-NMR (400 MHz, CDCl$_3$) δ: 0.69–0.79(2H, m), 0.83–0.97(2H, m), 1.43–1.53(1H, m), 1.45(9H, s), 1.68–1.77(1H, m), 3.49–3.52(1H, m), 3.70(3H, s), 3.79(1H, d, J=11.5 Hz), 3.88(1H, s), 4.00–4.03(1H, m), 4.16–4.22(1H, m), 4.23–4.25(1H, m), 4.76(1H, br.s), 4.96(1H, dm, J=62.7 Hz), 7.90(1H, d, J=13.7 Hz), 8.84(1H, d, J=2.44 Hz).

IR(KBr disk)cm$^{-1}$: 3450, 3415, 3082, 3001, 2976, 2935, 2881, 1716, 1631, 1568, 1525, 1444, 1365, 1331, 1286, 1257.

Melting point: 152–155° C.

Elementary analysis: on the basis of $C_{25}H_{28}BF_4N_3O_6$

Calculated: C, 54.27; H, 5.10; N, 7.59. Found: C, 54.12; H, 5.13; N, 7.41.

Specific rotation: $[α]_D^{19.7}$=−23.9° (c=1.00, CHCl$_3$)

Example 6

7-[(7S)-5-Aza-7-tert-butoxycarbonylaminospiro[2.4]heptan-5-yl]-6-fluoro-1-[(1R, 2S)-2-fluoro-1-cyclopropyl]-1,4-dihydro-8-methoxy-4-oxo-3-quinolinecarboxylic acid:

7-[(7S)-5-Aza-7-tert-butoxycarbonylaminospiro-[2.4]heptan-5-yl]-6-fluoro-1-[(1R, 2S)-2-fluoro-1-cyclopropyl]-1,4-dihydro-8-methoxy-4-oxo-3-quinolinecarboxylic acid difluoroboron chelate (1.47 g; 2.66 mmol) was dissolved in 80% hydrated ethanol (50 ml). Triethylamine (2 ml) was added thereto, and the resultant mixture was subjected to reflux for three hours. The solvent was evaporated under reduced pressure, and aqueous 10% citric acid solution (50 ml) was added to the residue. The mixture was extracted with chloroform (100 ml×2). The organic layer was washed with saturated brine (50 ml), and then dried over sodium sulfate, thereby removing the solvent. The residue was purified through recrystallization from a mixture of n-hexane and chloroform, followed by drying under reduced pressure, to thereby yield 1.37 g of the title compound as pale yellow crystals (quantitative yield).

$^1$H-NMR (400 MHz, CDCl$_3$)δ: 0.64–0.75(2H, m), 0.81–0.94(2H, m), 1.45(9H, s), 1.49–1.52(1H, m), 1.54–1.62(1H, m), 3.37(1H, d, J=10.5 Hz), 3.62(3H, s), 3.63–3.67(1H, m), 3.83–3.90(3H, m), 4.06–4.10(1H, m), 4.76–4.79(1H, m), 4.85(1H, dm, J=62.7 Hz), 7.83(1H, d, J=13.5 Hz), 8.70(1H, d, J=2.20 Hz).

IR(KBr disk)cm$^{-1}$: 3448, 3361, 3074, 2979, 2935, 2881, 1734, 1693, 1622, 1512, 1448, 1367, 1325, 1352, 1252.

Melting point: 167–169° C.

Elementary analysis: on the basis of $C_{25}H_{29}BF_2N_3O_6 \cdot 0.5H_2O$.

Calculated: C, 58.36; H, 5.88; N, 8.17.
Found: C, 58.50; H, 5.70; N, 8.17.

Specific rotation: $[α]_D^{19.7}$=−95.2° (c=0.930, CHCl$_3$)

Example 7

(−)-7-{(7S)-7-Amino-5-azaspiro[2.4]heptan-5-yl}-6-fluoro-1-[(1R, 2S)-2-fluoro-1-cyclopropyl]-1,4-dihydro-8-methoxy-4-oxo-3-quinolinecarboxylic acid (1):

7-[(7S)-5-Aza-7-tert-butoxycarbonylaminospiro-[2.4]heptan-5-yl]-6-fluoro-1-[(1R, 2S)-2-fluoro-1-cyclopropyl]-1,4-dihydro-8-methoxy-4-oxo-3-quinolinecarboxylic acid (1.37 g; 2.66 mmol) was dissolved by the addition of concentrated hydrochloric acid (5 ml) and 1N HCl (5 ml) on ice. The resultant solution was washed with chloroform (100 ml×3). The pH of the resultant acidic solution was adjusted to 11.0 in an ice bath with aqueous 10N NaOH solution. Subsequently, the pH of the obtained basic solution was adjusted to 7.4 with concentrated HCl and 1N HCl, followed by stirring for three hours at room temperature (pH after completion of stirring=7.4). Crystals precipitated were collected by filtration and dried under reduced pressure, to thereby yield 1.01 g of a crude form of the title compound as pale yellow crystals. The crystals were purified through recrystallization from a mixture of 28% ammonia water and ethanol, yielding 351 mg of the title compound as yellowish white crystals (yield: 33%).

$^1$H-NMR(400 MHz, 0.1N—NaOD)δ: 0.53–0.59(2H, m), 0.62–0.66(1H, m), 0.78–0.82(1H, m), 1.38–1.60(2H, m), 3.07(1H, s), 3.39(1H, dd, J=10.3, 26.0 Hz), 3.52(3H, s), 3.72(1H, d, J=10.0 Hz), 3.89–4.00(2H, m), 4.93(1H, dm, J=64.2 Hz), 7.62(1H, d, J=14.2 Hz), 8.43(1H, s).

Referential Example 7

Methanesulfonic Acid Salt of (−)-7-{(7S)-7-amino-5-azaspiro[2.4]heptan-5-yl}-6-fluoro-1-[(1R, 2S)-2-fluoro-1-cyclopropyl]-1,4-dihydro-8-methoxy-4-oxo-3-quinolinecarboxylic acid:

(−)-7-((7S)-7-Amino-5-azaspiro[2.4]heptan-5-yl)-6-fluoro-1-[(1R, 2S)-2-fluoro-1-cyclopropyl]-1,4-dihydro-8-methoxy-4-oxo-3-quinolinecarboxylic acid (1a) (2.51 g) was suspended in ethanol (20 ml). Methanesulfonic acid (1.2 equivalents) was added thereto, and the resultant mixture was stirred for five minutes at room temperature. Subsequently, diethyl ether (80 ml) was added thereto. Crystals precipitated were washed with diethyl ether, and collected through filtration (2.01 g, 94%).

The above-obtained crude crystals of methanesulfonic acid salt (900 mg) was dissolved in hot isopropanol (100 ml), and the solution was concentrated under heating until the volume of the entire solution became 40 ml. The concentrate was allowed to cool at room temperature, and crystals precipitated were collected through filtration, followed by washing with isopropanol, thereby yielding 720 mg of the title compound (yield: 80%).

Melting point: 257–258° C.

$^1$H-NMR(400 MHz, 0.1N—NaOD)δ: 0.58–0.72(3H, m), 0.80–0.90(1H, m), 1.40–1.62(2H, m), 2.82(3H, s), 3.10–3.12(1H, m), 3.41–3.49(2H, m), 3.58(3H, s), 3.81(1H, dd, J=2.44, 9.77 Hz), 4.85–4.93, 5.04–5.07(each 0.5H, m), 7.65(1H, d, J=14.16 Hz), 8.42(1H, s).

Test Example 1 (Confirmation of the Crystal Morphology of Compound (1))

Figure 2:
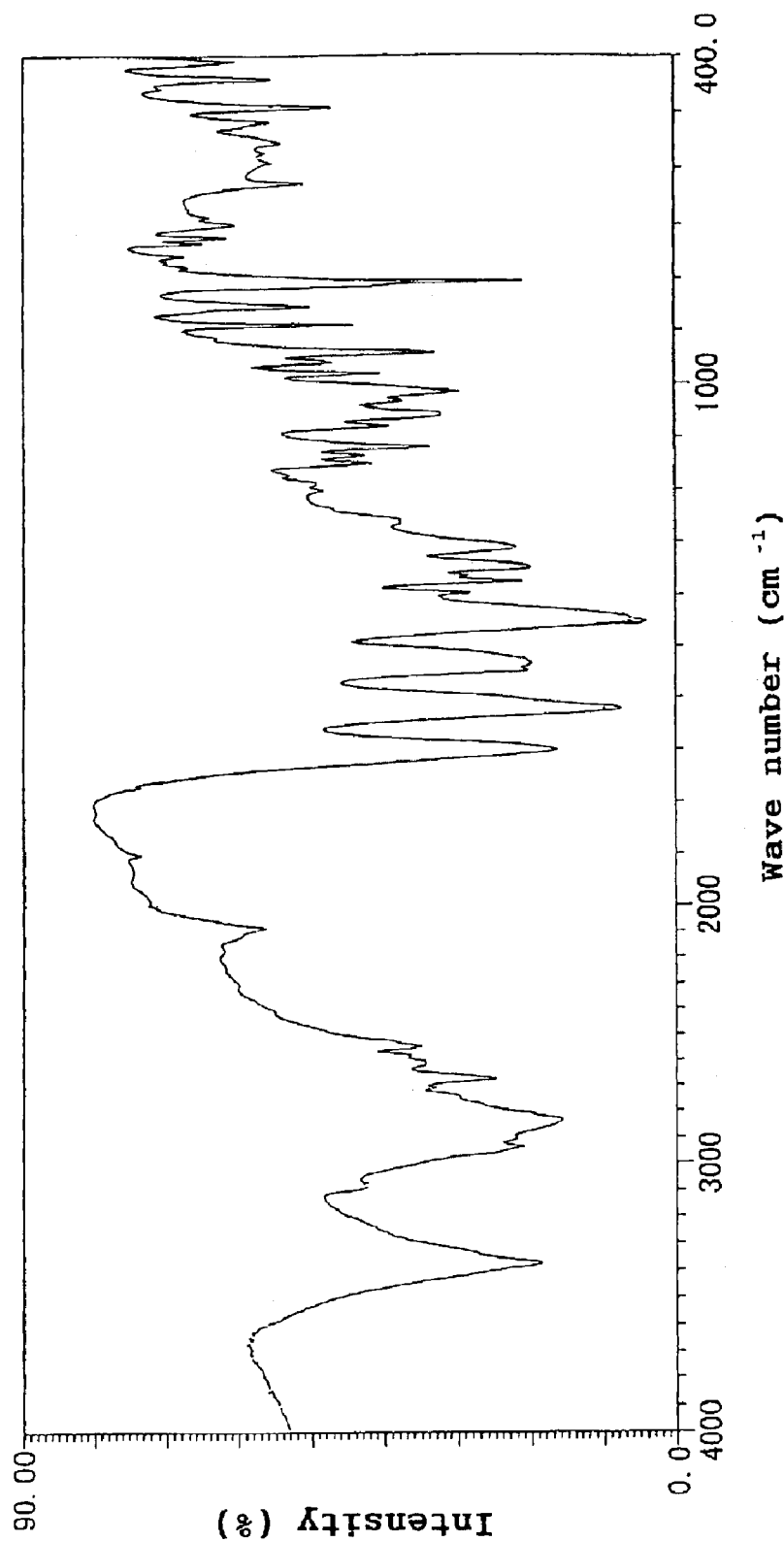
FIG. 2 shows an infrared absorption spectrum of compound (1).

(1) FIG. 1 shows the results of powder X-ray diffractometry of compound (1) (by means of an X'pert powder X-ray diffraction apparatus, product of Philips), and FIG. 2 shows the IR spectrum of compound (1) (obtained using model FT-720, FT-IR, product of HORIBA). Thermal analysis of compound (1) revealed that the weight loss was 4.2% by weight, which was in agreement with the theoretical value (3.9%) of monohydrate.

(2) Quantitative analysis by the Karl Fischer's method revealed that the water content of compound (1) is 4.11%, which is in agreement with the result of thermal analysis.

Test Example 2

Figure 3:
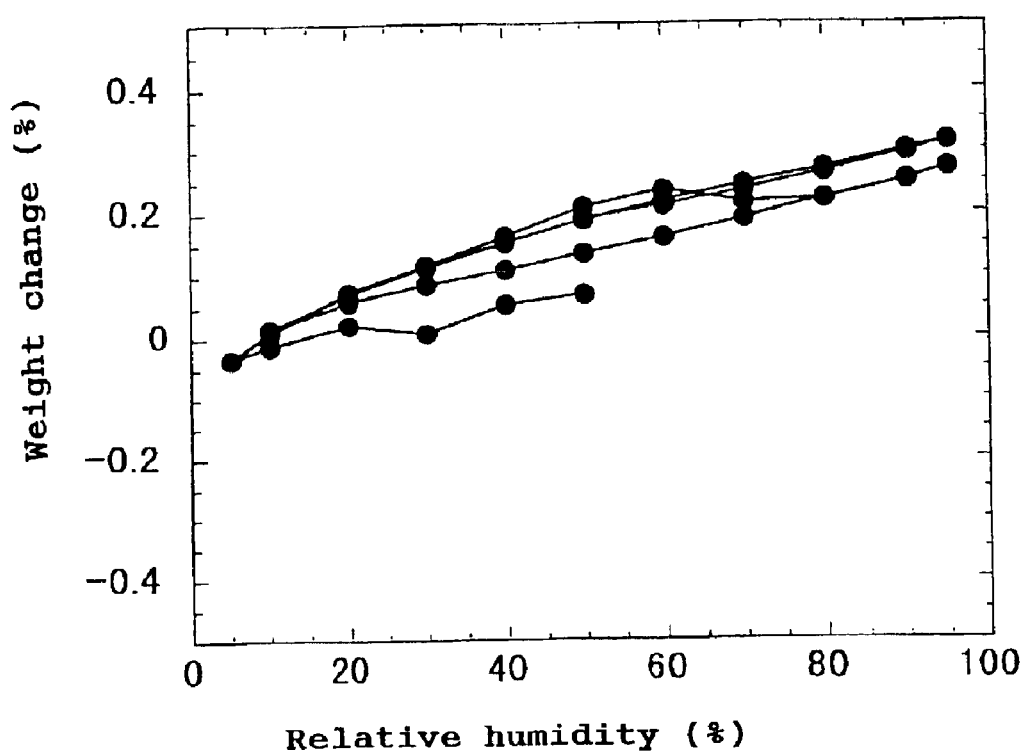
FIG. 3 is a graph showing the weight change of compound (1) under 5–95% RH.

Moisture absorption/desorption of compound (1) was investigated by using samples each weighing approximately 10 mg and a moisture absorption analyzer manufactured by VTI (model SGA-100). The measurement was performed at 25° C., and the relative humidity was changed in the range of 5% to 95% at intervals of 5% or 10%. When the weight change of a sample is 0.03% or less within 30 minutes, the sample is considered to be in a state of equilibrium, and in this test, the longest equilibrium time was set to be 180 minutes. The weight change of each sample at different relative humidities was determined. As a result, as shown in FIG. 3, compound (1) was found to be stable, neither absorbing or desorbing moisture within the relative humidity range of 5–95% RH.

Test Example 3

Acid addition salts of compound (1a) (methanesulfonic acid salt, p-toluenesulfonic acid salts, citric acid salt, and malic acid salt) were prepared, and their stability under various levels of humidity was evaluated. All the tested salts showed a tendency toward moisture absorption under high-humidity conditions. In the meantime, although attempts were made to prepare an acetic acid salt and a lactic acid salt of compound (1a), no salt was formed.

Test Example 4

Solubility of compound (1) in water was investigated. Compound (1) was found to have a high solubility in water; i.e., 100 mg/mL or more.

Test Example 5

Compound (1) (1.5 mg) was stored for one week under the following conditions: (1) in a sealed bottle at 70° C., (2) in an open-air state at 50° C., 75% RH (NaCl), or (3) irradiation with light at 100,000 lx·h (2,500 lx×40 h). Subsequently, the residual amount of compound (1) was quantitatively determined by means of liquid chromatography. Results are as follows: Compound (1) remained stable, not undergoing any decomposition, even when exposed to light irradiation. Moreover, the stability of compound (1) when exposed to light was superior to that of compound No. 26bb disclosed in Japanese Patent No. 2714597.

Test Example 6

Slc:ddY mice (male; 3 weeks old) were used in groups of ten. Compound (1) was dissolved in distilled water in order to prepare injections, and the resultant solution was cisternally administered in a volume of 5 μg/mouse. To the members of the group where compound (1) and biphenylacetic acid were used in combination, biphenylacetic acid (400 mg/kg) was perorally administered first, and 30 minutes following the administration, compound (1) was cisternally administered in a manner similar to that employed for the single use of compound (1).

The results are as follows: In both cases of solo administration of compound (1) and combined administration of compound (1) and biphenylacetic acid, compound (1) caused neither spasm nor death and was proven to have very weak central toxicity. Thus, compound (1) is a very safe compound.

In contrast, administration of comparative compound A at the same dose induced spasm in two mice out of ten. Also, there was one death among the ten mice. Moreover, in the case of combined administration with biphenylacetic acid as described above, there were four spasm cases and two deaths out of 10 mice.

Comparative Compound A:

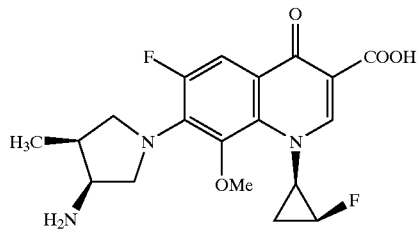

Test Example 7

Groups of young beagles (male; 3–4 months old), each group consisting of 3 dogs, were used in the test. Compound (1) was perorally administered to each dog for eight days. Thereafter, important diarthroses were pathologically examined. Results: Members of the groups to which compound No. 26bb disclosed in Japanese Patent No. 2714597 was administered at high doses of 14.1 mg/kg or more showed formation of blebs or erosions in arthrodial cartilage, whereas in the compound (1) administration groups (7.5 mg/kg, 15 mg/kg, and 30 mg/kg), formation of blebs or erosions was not at all observed. Thus, articular toxicity of compound (1) is quite weak and insignificant, proving that compound (1) is a very safe compound.

Test Example 8

Groups of Balb/c mice (female; 5 weeks old), each group consisting of 5–6 mice, were used in the test. After compound (1) was intravenously administered to each mouse, the mouse was exposed to long-wavelength UV light (UV-A) (20 J/cm$^2$) for four hours. Thereafter, the auricle was visually observed for 96 hours. Subsequently the mouse was sacrificed for examination of the tissue. In the groups where compound (1) was administered at (100 mg/kg), no abnormality was observed either during visual observation or at the time of tissue examination. Thus, compound (1) is a very safe compound, being free from phototoxicity, which is often observed with quinolone-based antibacterial agents.

Test Example 9

(1) Therapeutic Effect on Mouse Pneumonia Model by Use of Pneumococcus of Low Penicillin Sensitivity:

Groups of CBA/J mice, each group consisting of 5 mice, were used in the test. The mice were nasally infected with pneumococcus SPI-13 at 5.3×10$^6$ CFU/mouse. Compound (1) was subcutaneously administered to each mouse at doses of 7.5 mg/kg, 15 mg/kg, or 30 mg/kg, for three consecutive days from the day following infection, twice a day at an interval of 6 hours. The efficacy of compound (1) was assessed by counting the number of the intrapulmonary bacteria on the day following the final administration. Results: At a dose of 30 mg/kg or 15 mg/kg, compound (1) reduced the bacterial count to below the detection limit, and at a dose of 7.5 mg/kg, reduced the bacterial count to approximately half that of the control.

(2) Infection-preventing Effect on Mouse Sepsis Model.

Groups of Slc:ddY mice, each group consisting of 7 mice, were used in the test. The mice were intraperitoneally inoculated with methicillin-resistant *Staphylococcus aureus* (MRSA) strain 7866 (1.07×10$^8$ CFU/mouse) or *E. coli* strain E77156 (8.08×10$^7$ CFU/mouse). Compound (1) was given as a single injection into the tail vein of each mouse immediately after infection. On the basis of the survival count on day 7 after infection, 50% efficacy was calculated using the probit method, to thereby evaluate the efficacy. Results: The 50% efficacy of compound (1) against MRSA strain 7866 was found to be 3.34 mg/kg, and the same efficacy against *E. coli* strain E77156 was found to be 0.57 mg/kg.

From (1) and (2) above, it can be concluded that compound (1) has excellent preventive and therapeutic effects against different infectious diseases when tested in vivo.

Test Example 10 (Antibacterial Activity)

Antibacterial activity was investigated by comparing compound (1) with comparative compounds B and C (see next page). This test was performed according to the standard method recommended by Japanese Society of Chemotherapy. The test results are shown in Table 1.

TABLE 1

| | Antibacterial Activity MIC(μg/mL) | | |
|---|---|---|---|
| | Compound (1) | Comparative Compound B | Comparative Compound C |
| E. coli, NIHJ | ≦0.003 | 0.006 | 0.025 |
| Pr. vulgaris, 08601 | 0.012 | 0.05 | 0.05 |
| Ser. marcescens, 10100 | 0.05 | 0.20 | 0.20 |
| Ps. aeruginosa, 32104 | 0.20 | 0.39 | 0.78 |
| Ps. aeruginosa, 32121 | 0.05 | 0.20 | 0.39 |
| S. aureus, 209P | 0.006 | 0.025 | 0.05 |

TABLE 1-continued

| | Antibacterial Activity MIC(μg/mL) | | |
|---|---|---|---|
| | Compound (1) | Comparative Compound B | Comparative Compound C |
| S. epidermidis, 56500 | 0.05 | 0.10 | 0.20 |
| Str. faecalis, ATCC 19433 | 0.10 | 0.20 | 0.39 |

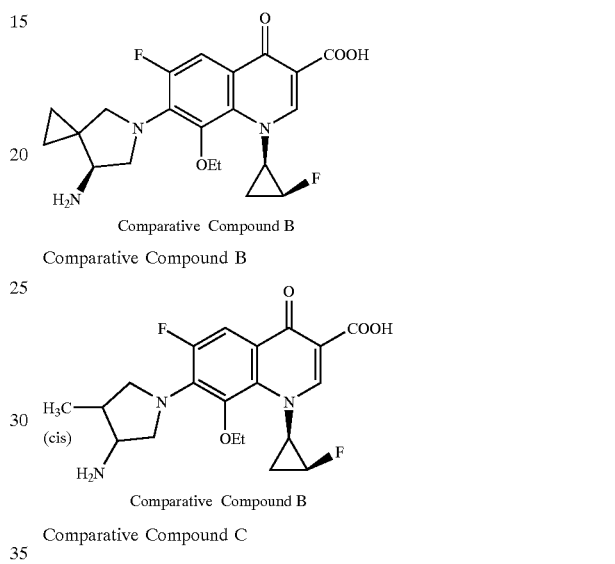

Comparative Compound B

Comparative Compound C

The compounds of the present invention are endowed with excellent antibacterial activity and safety, and also are very stable against light or humidity, thereby finding utility as antibacterial agents.

What is claimed is:

1. A compound represented by the following formula (1)

(1)

·1HCl·1H$_2$O ·

2. A compound as claimed in claim 1, which assures crystals exhibiting characteristic peaks in the vicinity of angles of diffraction (2θ) of 6.9, 10.5, 14.4, 23.1, 26.9, and 27.8(°) when subjected to powder X-ray diffractometry.

3. A solid antibacterial composition containing a compound represented by the following formula (1) together with a pharmaceutically acceptable carrier

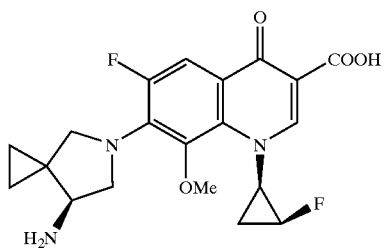

·1HCl·1H₂O ·   (1)

4. A solid antibacterial composition as claimed in claim 3, wherein the compound of formula (1) assumes crystals exhibiting characteristic peaks in the vicinity of angles of diffraction (2 θ) of 6.9, 10.5, 14.4, 23.1, 26.9, and 27.8(°) when subjected to powder X-ray diffractometry.

5. A method for the treatment of bacterial infection in a mammal or fish, which comprises administering to said mammal or fish an effective amount of a compound represented by the following formula (1)

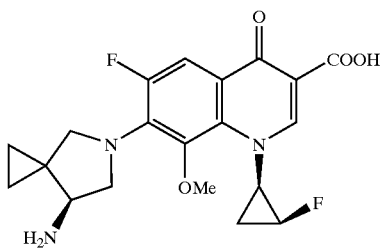

·1HCl·1H₂O ·   (1)

6. The method as claimed in claim 5, wherein the compound of formula (1) assumes crystals exhibiting characteristic peaks in the vicinity of angles of diffraction (2 θ) of 6.9, 10.5, 14.4, 23.1, 26.9, and 27.8(°) when subjected to powder X-ray diffractometry.

* * * * *